US012064138B2

(12) United States Patent
Wang

(10) Patent No.: US 12,064,138 B2
(45) Date of Patent: Aug. 20, 2024

(54) PUNCTURE GUIDER AND PUNCTURE GUIDING SYSTEM

(71) Applicant: Qin Wang, Jiangsu (CN)

(72) Inventor: Qin Wang, Jiangsu (CN)

( * ) Notice: Subject to any disclaimer, the term of this patent is extended or adjusted under 35 U.S.C. 154(b) by 816 days.

(21) Appl. No.: 17/254,181

(22) PCT Filed: Jun. 21, 2018

(86) PCT No.: PCT/CN2018/092139
§ 371 (c)(1),
(2) Date: Dec. 18, 2020

(87) PCT Pub. No.: WO2019/241949
PCT Pub. Date: Dec. 26, 2019

(65) Prior Publication Data
US 2021/0259726 A1  Aug. 26, 2021

(51) Int. Cl.
*A61B 17/34* (2006.01)
(52) U.S. Cl.
CPC .................. *A61B 17/3403* (2013.01)
(58) Field of Classification Search
CPC ........ A61B 17/3403; A61B 2017/3405; A61B 2017/345; A61B 2017/347; A61M 5/46
See application file for complete search history.

(56) References Cited

U.S. PATENT DOCUMENTS 6,296,614 B1   10/2001  Pruter
7,452,331 B1 *  11/2008  Pruter ................ A61B 17/3403
                                                          600/585

(Continued)

FOREIGN PATENT DOCUMENTS

CN       1575776 A      2/2005
CN     101756715 A      6/2010
(Continued)

OTHER PUBLICATIONS

English Translation CN205359580 (Year: 2016).*
(Continued)

*Primary Examiner* — Darwin P Erezo
*Assistant Examiner* — Erin L Colello
(74) *Attorney, Agent, or Firm* — James H. Ortega; David W. Carstens; Carstens, Allen & Gourley, LLP

(57) ABSTRACT

Disclosed are a puncture guider (02, 2) and a puncture guiding system, wherein a puncture channel (80) automatically adapted to the diameter of a puncture needle (03) can be realized in the puncture guider (02, 2). The puncture guider (02, 2) is used for connecting to a puncture support, and the puncture guider (02, 2) comprises a depth block (21) and a push plate (22), wherein the depth block (21) comprises: a connection structure for being connected to the puncture support, and a first guiding wall (211) and a second guiding wall (212), which are connected to each other and form an included angle; and the push plate (22) comprises: a needle groove plate (222), and an adaptive component. A first end face (2221) of the needle groove plate (222), and the first guiding wall (211) and the second guiding wall (212) enclose a puncture channel (80), and under the action of the adaptive component, a displacement can occur between the first end face (2221) of the needle groove plate (222) and the first guiding wall (211) and second guiding wall (212), so that the puncture channel (80) can change automatically according to the specification of the puncture needle (03), thereby automatically adapting to puncture needles (03) with different needle diameter specifications. The puncture guiding system comprises a puncture support and a puncture guider (02, 2).

10 Claims, 7 Drawing Sheets

(56) References Cited

U.S. PATENT DOCUMENTS

| | | | | |
|---|---|---|---|---|
| 2005/0131291 A1* | 6/2005 | Floyd | ................ | A61B 17/3403 |
| | | | | 600/424 |
| 2005/0143753 A1* | 6/2005 | Whitmore | .............. | A61B 90/11 |
| | | | | 606/130 |
| 2015/0112200 A1* | 4/2015 | Oberg | ................. | A61B 8/4455 |
| | | | | 600/461 |

FOREIGN PATENT DOCUMENTS

| | | | | |
|---|---|---|---|---|
| CN | 202397562 U | | 8/2012 | |
| CN | 203425000 U | * | 2/2014 | |
| CN | 203425000 U | | 2/2014 | |
| CN | 205359580 U | * | 7/2016 | |
| CN | 205359580 U | | 7/2016 | |
| WO | WO-2006060657 A2 | * | 6/2006 | ........... A61B 8/0833 |

OTHER PUBLICATIONS

English Translation CN203425000 (Year: 2014).*
Machine Translation of CN203425000.
Machine Translation of CN205359580.
Machine Translation of CN1575776.
Machine Translation of CN202397562.
Machine Translation of CN101756715.

* cited by examiner

PUNCTURE GUIDER AND PUNCTURE GUIDING SYSTEM

TECHNICAL FIELD

The present invention relates to the technical field of medical instruments, and in particular to a puncture guider and a puncture guiding system.

BACKGROUND

With the development of medical science and nursing science, infusion tools are developed from simple scalp needles to the choices of various infusion tools, such as venous indwelling needles, infusion ports, PiCCs, and the like, so surgeons need to master the application of various infusion tools to increase the daily work efficiency and nursing skills. At present, PICC (Peripherally Inserted Central Catheterization), as a kind of auxiliary infusion tool, is being popularized and applied clinically at an unprecedented speed. Intravenous catheterization is usually performed under ultrasound images to insert an infusion catheter into a vein by utilizing the puncture guiding function of a puncture support.

At present, a puncture using an ultrasound image with the puncture support is mainly divided into two types: in-plane puncture and out-of-plane puncture. The in-plane puncture refers to a puncture process in which a puncture needle guided by the puncture support is inserted within a sound beam from ultrasound, and the out-of-plane puncture refers to a puncture process in which a puncture needle guided by the puncture support is wholly or partially inserted outside a sound beam from ultrasound. A path of a puncture needle can be displayed in real time during the in-plane puncture, and position of a needle tip can be accurately seen. For the out-of-plane puncture, an inserting position along the lateral center line of a probe is generally preferred out of many relatively complicated paths, the target area is displayed in the middle of an ultrasonic scanning range, the position of the probe is fixed, and the puncture needle penetrates skin from the lateral side of the probe. The position of the needle tip cannot be seen due to a too large blind-spot distance, so the puncture depth and the distance off from the target depth can only be acknowledged by shaking back and forth during insertion. The insertion is ended when the puncture needle returns blood or reaches the target position. Therefore, the existing defects are obvious: the target position cannot be effectively and quickly reached, and multiple needle insertions are needed when single insertion has poor accuracy. In addition, the sizes of the puncture needles required by different puncture operations are different, so that a surgeon needs to select a needle groove matched with the diameter specification of the puncture needle to meet the requirements of the operation every time the operation is performed. According to a prior-art method, the puncture support comes with needle groove plates having various specification diameters for surgeons to select, and the needle groove plates not selected are wasted. This causes an increase in the usage of surgical consumables, an increase in the economic burden of a patient, and an extension in the surgical time.

SUMMARY

In view of this, the present invention provides a puncture guider and a puncture guiding system, capable of realizing a puncture channel adaptive to a puncture needle diameter in the puncture guider. Other objectives and beneficial effects of the present invention are described or embodied with reference to specific embodiments.

To achieve the foregoing objective, according to an aspect of the present invention, a puncture guider is provided.

The puncture guider of the present invention for connecting to a puncture support includes a depth block and a push plate, wherein the depth block includes: a connection structure for being connected to the puncture support; and a first guiding wall and a second guiding wall, which are connected to each other and form an included angle; and the push plate includes: a needle groove plate; and an adaptive component, where a first end face of the needle groove plate encloses a puncture channel with the first guiding wall and the second guiding wall, and under an action of the adaptive component, a displacement can occur between the first end surface of the needle groove plate and the first guiding wall and second guiding wall, so that the puncture channel can change automatically according to a specification of a puncture needle, thereby automatically adapting to puncture needles with different needle diameter specifications.

Optionally, the adaptive component is an elastic component.

Optionally, the connection structure includes a cylindrical ridge and two mounting walls parallel to each other, where the cylindrical ridge can be connected to a groove on the puncture support; the second guiding wall is located at a first side of the first guiding wall, is perpendicular to the first guiding wall and is perpendicular to a first edge of the first guiding wall; the cylindrical ridge is parallel to and connected to the first edge of a second side of the first guiding wall; and the mounting walls extend from the second side of the first guiding wall in a direction away from the first guiding wall.

Optionally, one or two of the mounting walls are provided with a protuberance, and the protuberance can be connected to a groove or an indentation on the puncture support.

Optionally, the elastic component comprises a tension plate and an elastic wall, where the tension plate is fixedly connected to the needle groove plate through two connection rods, and the tension plate, the needle groove plate and the connection rod form a rectangle; and a first end of the elastic wall is connected to the tension plate, where an opposite end of the first end abuts against the first side of the first guiding wall, a push force of the elastic wall points to a second side of the second guiding wall, and the puncture channel is located at the second side of the second guiding wall.

Optionally, two of the elastic walls are provided in a shape of a pair of brackets.

Optionally, the first end surface of the needle groove plate is an inclined plane in a shape of a slope, thereby enclosing a puncture channel having a triangular cross section with the first guiding wall and the second guiding wall.

According to another aspect of the present invention, a puncture guiding system is provided.

The puncture guiding system of the present invention includes a puncture support and the puncture guider in the present invention, and the puncture support includes an annular puncture support body and at least one hook fixed on the puncture support body; and the hook is configured to cooperate with a connection structure on the puncture guider to connect the puncture guideron the puncture support.

Optionally, each of two ends at an opening of the puncture support is provided with a connecting port; the puncture guiding system further includes a lock for connecting to both the two connecting ports in a non-detachable manner, so that the puncture support is formed into a closed ring shape; and the lock is provided with a weakpart, where the lock can be torn apart from the weakpart, thereby destroying the puncture support.

Optionally, the weakpart is formed by one or more rows of spaced holes on the lock.

Optionally, a top of the hook is provided with a groove, capable of rotationally connecting to a cylindrical ridge of the puncture guider; two hook walls parallel to each other are provided under the top of the hook, and are perpendicular to an extending direction of the groove in the top of the hook; and the hook wall is provided with a U-shaped groove, capable of slidably connecting to a protuberance on amounting wall of the puncture guider.

Optionally, atop of each hook is provided with a groove, capable of rotationally connecting to a cylindrical ridge of the puncture guider; two hook walls parallel to each other are provided under the top of the hook, and are perpendicular to an extending direction of the groove in the top of the hook; and the hook wall is provided with an indentation, capable of fixedly connecting to the protuberance on the mounting wall of the puncture guider.

According to the technical solutions of the present invention, the needle groove plate has an elastic component, capable of forming a puncture channel having a size adaptive to the needle diameter of the puncture needle. Mounting walls on depth blocks of the different puncture guiders may be differed, thereby achieving puncture channels at various angles. The design of perpendicularity of the first guiding wall and the second guiding wall facilitates an operator to drive the first guiding wall with his fingers to open the puncture channel, so that the puncture needle can be easily taken out of the puncture channel.

BRIEF DESCRIPTION OF DRAWINGS

The accompanying drawings are intended to provide a better understanding of the present invention, and constitute no inappropriate limitation on the present invention. In the drawings.

DETAILED DESCRIPTION OF THE INVENTION

The following describes exemplary embodiments of the present invention with reference to the accompanying drawings, in which various details of the embodiments of the present invention are included to facilitate understanding, and which are to be considered as exemplary only. Accordingly, a person of ordinary skill in the art shall appreciate that various changes and modifications can be made to the embodiments described herein without departing from the scope and spirit of the present invention. Likewise, for clarity and conciseness, descriptions of well-known functions and structures are omitted from the following description.

Figure 1:
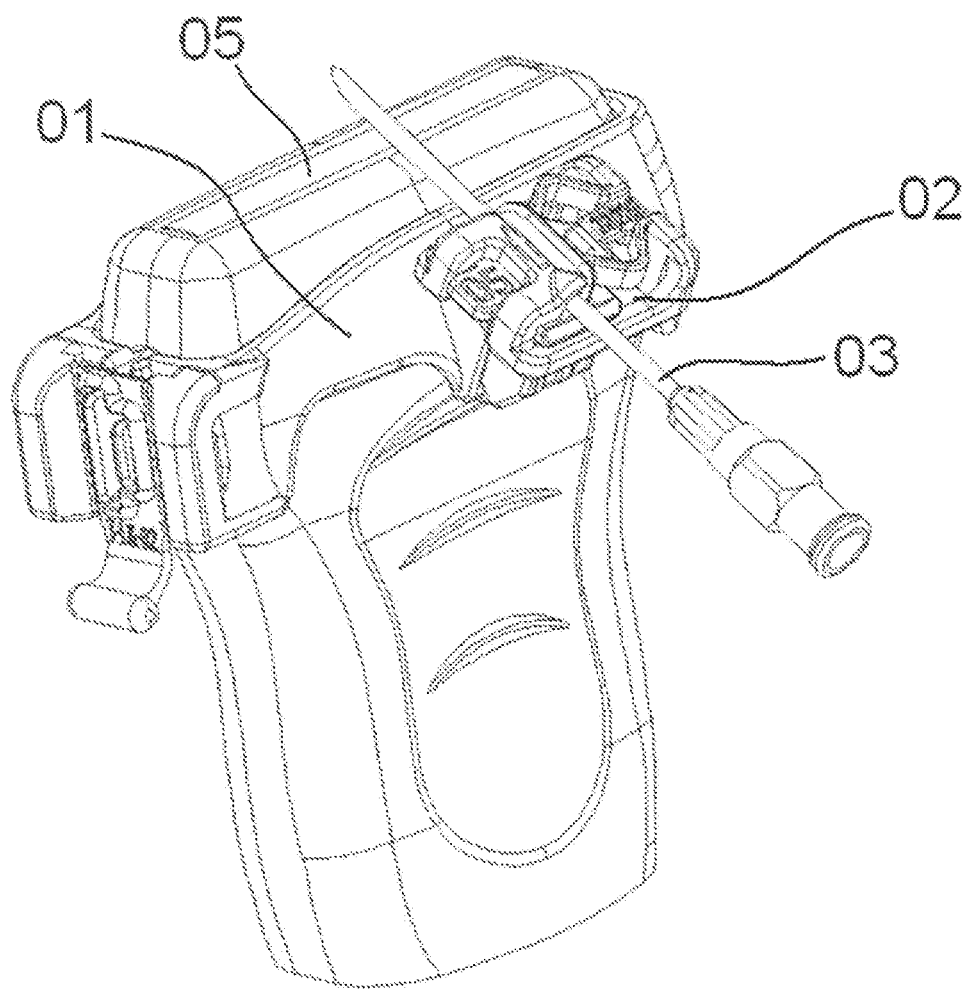
FIG. 1 is a schematic diagram of an application state of a puncture guiding system according to an embodiment of the present invention.

FIG. 1 is a schematic diagram of an application state of a puncture guiding system according to an embodiment of the present invention. As shown in FIG. 1, an annular puncture support body 01 is sleeved on an ultrasonic probe 05, a puncture guider 02 is fixed on the puncture frame body, and a puncture needle 03 passes through a puncture channel in the puncture guider 02. FIG. 1 shows a state of an out-of-plane puncture. If the position of the puncture guider 02 on the puncture support body 01 is changed, the puncture guider is also suitable for an in-plane puncture.

Figure 2:
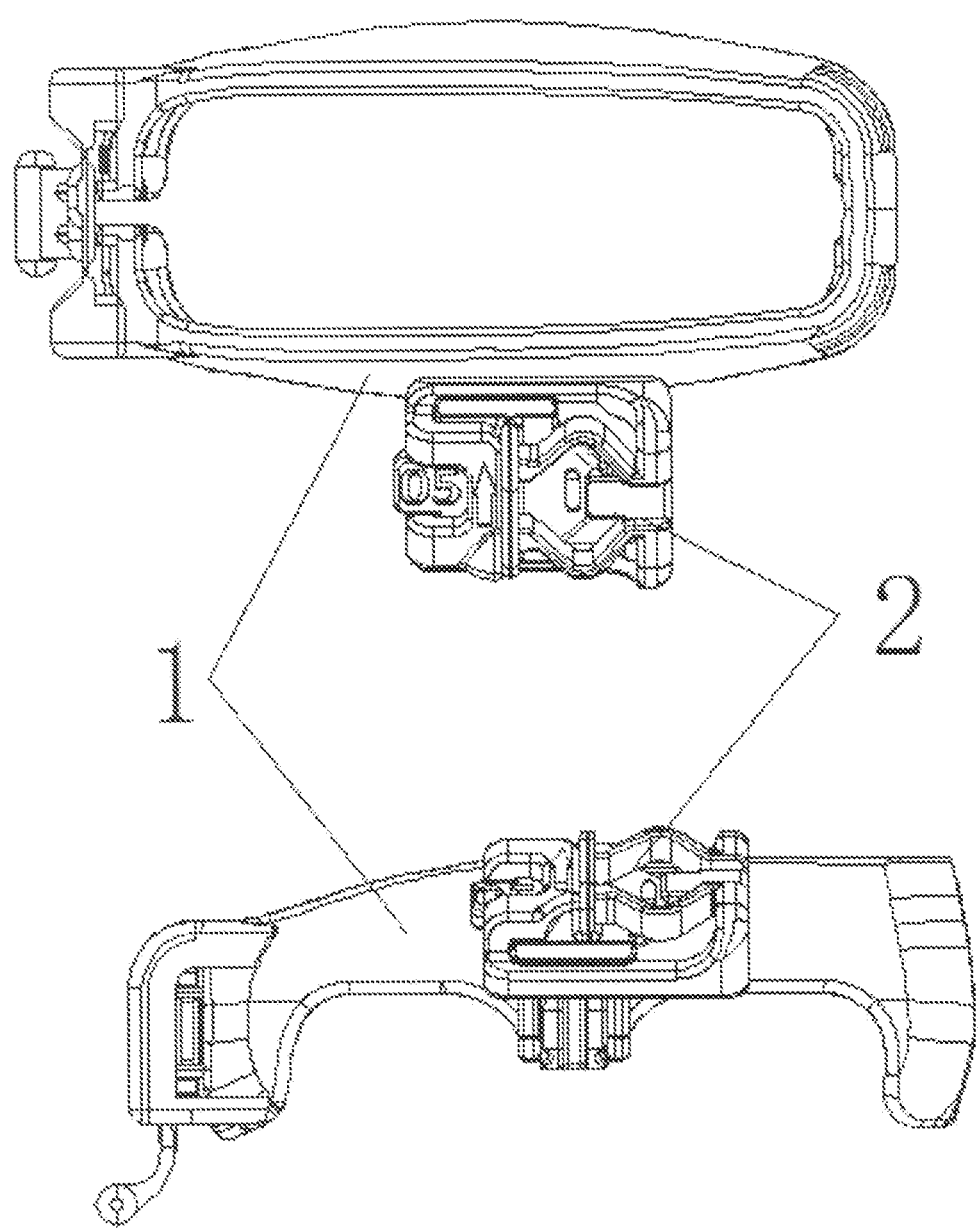
FIG. 2 is a schematic diagram of an assembled state of a puncture guiding system according to an embodiment of the present invention.

FIG. 2 is a schematic diagram of an assembled state of a puncture guiding system according to an embodiment of the present invention. As shown in FIG. 2, a top view of the puncture guiding system is provided on top, and a front view of the puncture guiding system is provided on bottom, where a puncture guider 2 is mounted on an annular puncture support body 1. The figure shows a case in which one puncture guider is mounted, and a plurality of puncture guiders can also be mounted on the puncture support body during application.

Figure 3:
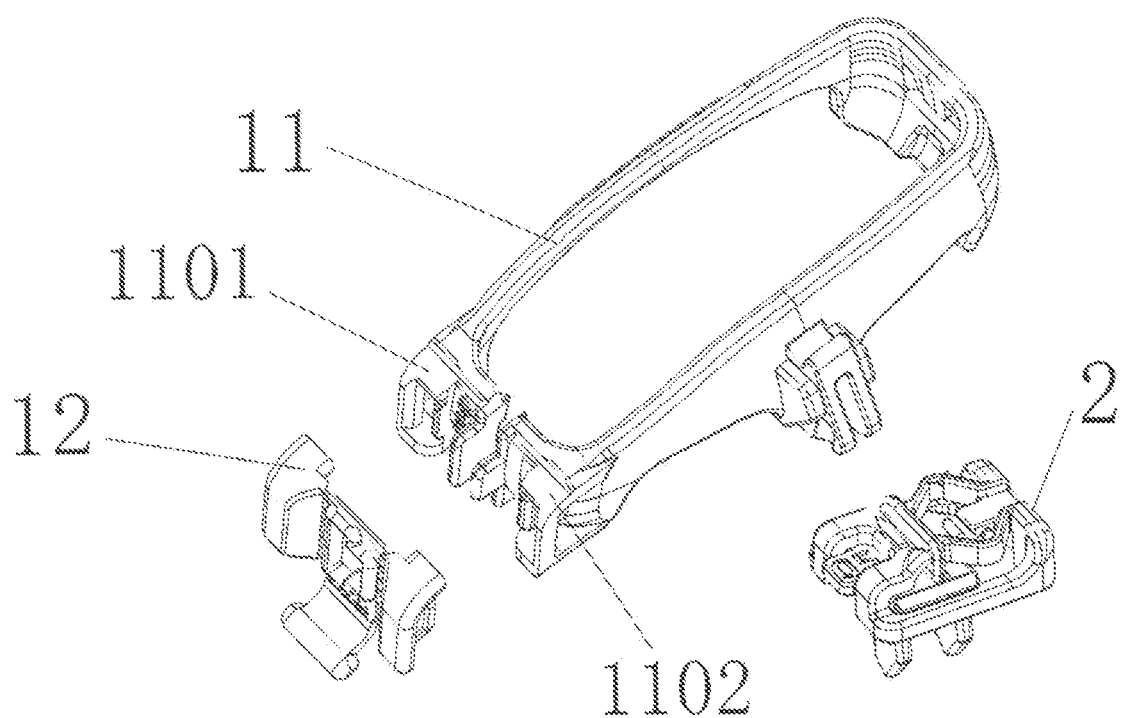
FIG. 3 is a schematic diagram of an exploded state of a puncture guiding system according to an embodiment of the present invention.

FIG. 3 is a schematic diagram of an exploded state of a puncture guiding system according to an embodiment of the present invention. The puncture guiding system has a puncture support body 11 and a puncture guider 2. For convenience of mounting, the puncture support body can be provided with an opening, two ends of the opening are provided with a connecting port 1101 and a connecting port 1102 respectively, and the two connecting ports can be locked together by using a lock 12, thereby forming a closed ring shape. The connection manner of the lock 12 at the opening may be non-detachable. For example, both the lock 12 and the opening have barbs (see for example connection fastener 112 in FIG. 4), and after hooking to each other, the barbs of the lock 12 and the opening are covered in the lock 12 and unable to be detached. In addition, the lock 12 can be provided with a weakpart, for example, one or more rows of spaced holes, similar to the holes in a stamp or the holes in other shapes, so that the lock 12 can be torn from the positions of these holes, thereby destroying the puncture support.

Figure 4:
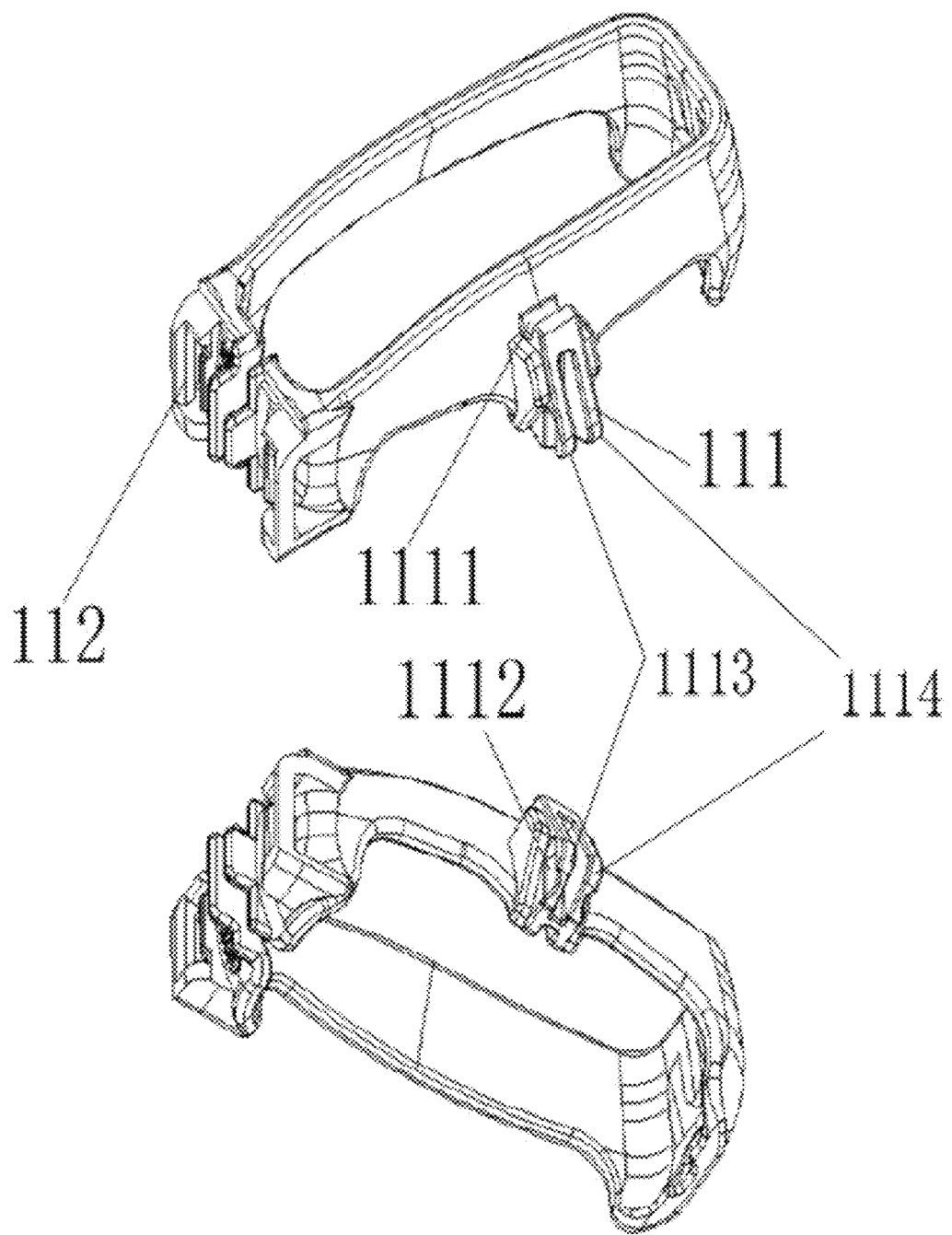
FIG. 4 is a schematic diagram of a puncture support body and a puncture guider according to an embodiment of the present invention.

FIG. 4 is a schematic diagram of a puncture support body and a puncture guider according to an embodiment of the present invention. As shown in FIG. 4, the puncture support body has a connection fastener 112, and the top of hook 111 has a cylindrical groove 1111. A hook wall 1113 and a hook wall 1114 parallel to each other are provided under the top of the hook 111, and are perpendicular to an extending direction of the groove 111. The hook wall 1113 and the hook wall 1114 may be provided with a U-shaped groove 1112, as shown in the figure, or may be provided with an indentation (not shown in the figure).

Figure 5:
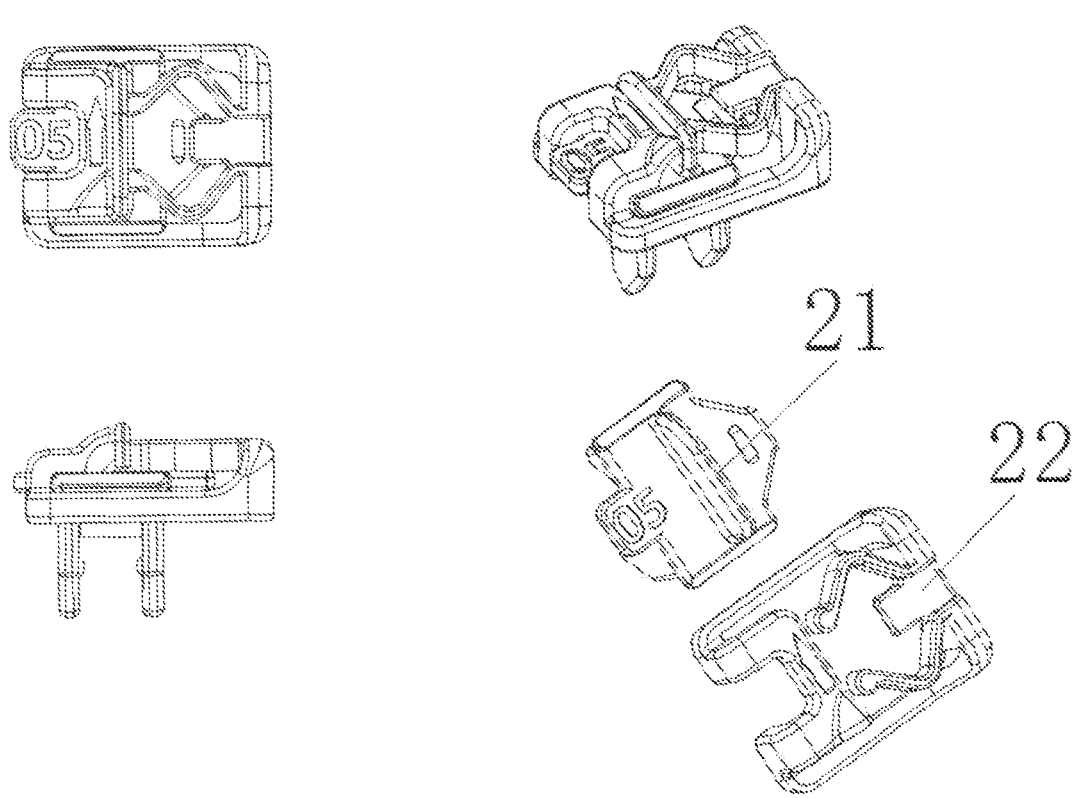
FIG. 5 is a schematic diagram of a puncture guider according to an embodiment of the present invention.

FIG. 5 is a schematic diagram of a puncture guider according to an embodiment of the present invention. For convenience of viewing, many views of the puncture guider are shown together in FIG. 5, where the left upper view and lower view are respectively a top view and a front view of the puncture guider, the right upper view is a perspective view, and the right lower view shows an exploded state of the puncture guider. As shown in the figure, the puncture guider includes a depth block 21 and a push plate 22. The following further describes specific structures of the depth block 21 and the push plate 22.

Figure 6:
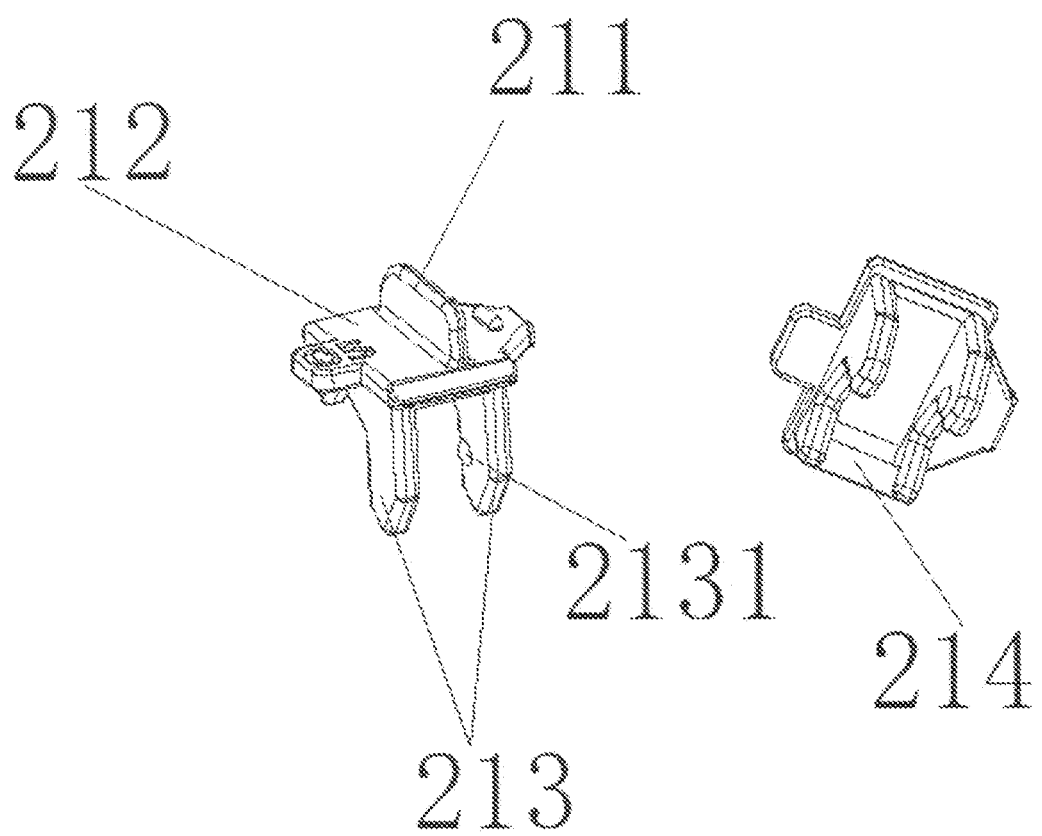
FIG. 6 is a schematic diagram of a structure of a depth block according to an embodiment of the present invention.

FIG. 6 is a schematic diagram of a structure of a depth block according to an embodiment of the present invention. For convenience of viewing, two prospective views of the depth block are shown in FIG. 6. As shown in the left view in FIG. 6, the depth block includes a first guiding wall 211 and a second guiding wall 212 which are connected to each other and form an included angle (shown as a right angle in the figure). According to the views in the figure, the first guiding wall 211 is located above the second guiding wall 212 and the two are perpendicular to each other, two mounting walls 213 are below the second guiding wall 212 and extend downward, and one or both of the mounting walls 213 can be provided with a protuberance 2131. Referring again to the right view in FIG. 6, a cylindrical ridge 214 is parallel to an edge of the second guiding wall 212 and is connected to the edge, and the cylindrical ridge 214 and the first guiding wall 211 are separately located at the two sides of the second guiding wall 212.

Cooperating with the structure of shook 111 on a puncture support, the cylindrical ridge 214 and the two mounting walls 213 may achieve a connection between the depth block and the puncture support, that is, the two forms a connection structure. Specifically, the cylindrical ridge 214 is rotationally connected to a cylindrical groove 1111 on the top of the hook 111; if the protuberance 2131 and a groove or an indentation on the hook wall 1114 are absent, the mounting walls and the hook walls are attached by friction. The present invention is not limited to the forgoing several embodiments, and the depth block and the puncture support may be connected in other manners during implementing.

In the embodiment of the present invention, the cylindrical groove 1111 is matched with the cylindrical ridge 214 to form a rotary connection, and mounting walls with various lengths may be equipped. This facilitates formation of puncture channels at various angles (see FIG. 1, where the angle is an included angle between a puncture needle 03 and a horizontal plane), so that a puncture depth can be adjusted.

Figure 7:
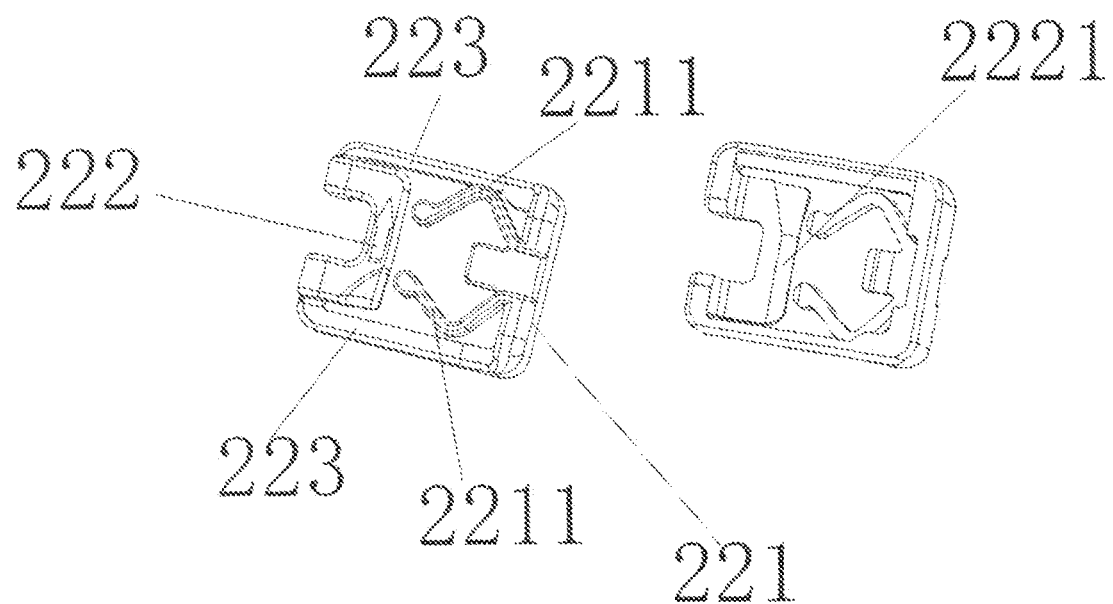
FIG. 7 is a schematic diagram of a push plate according to an embodiment of the present invention.

FIG. 7 is a schematic diagram of a push plate according to an embodiment of the present invention. As shown in FIG. 7, the push plate is in a rectangular shape in its entirety, including a tension plate 221, two elastic walls 2211, a needle groove plate 222, and two connection rods 223. Connection relationships are shown in the figure, that is, one end of the two elastic walls 2211 are connected to the tension plate 221, while the tension plate 221 is connected to the needle groove plate 222 through the two connection rods 223. The push plate in the left view in FIG. 7 is a state in the right view after being turned over. Referring to the right view, a first end surface 2221, close to the elastic walls 2211, of the needle groove plate 222 is an inclined plane 2221 in a shape of a slope, so that when a depth block and the push plate are assembled together, a section of a puncture channel is triangular. The following provides further description with reference to FIG. 8.

Figure 8:
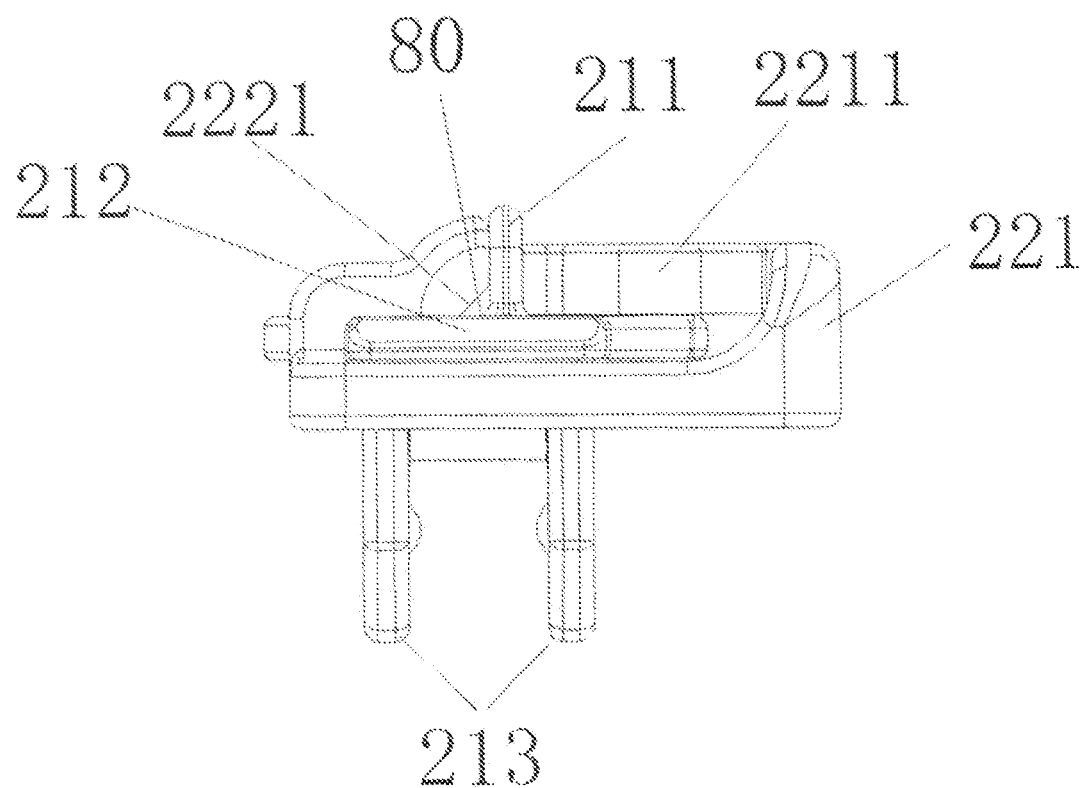
FIG. 8 is a front view of a puncture guider according to an embodiment of the present invention.

FIG. 8 is a front view of a puncture guider according to an embodiment of the present invention. As shown in FIG. 8, a first guiding wall 211, a second guiding wall 212 and an inclined plane 2221 enclose a puncture channel 80. A resilient force produced by an elastic component composed of a tension plate 221 and two elastic walls 2211 points to the left according to the view in the figure, that is, a push force points to a needle groove plate 222. Therefore, a size or a thickness of the puncture channel 80 may alter to a certain extent. When a puncture needle is inserted to the puncture channel (see the left upper view in FIG. 5, where a direction of an upward arrow to the right of a numeral 05 is an insertion direction), the first guiding wall 211 can be squeezed to the right in the figure. Moreover, under the action of the above-mentioned push force, the first guiding wall 211 and the inclined plane 2221 may be kept in a state of clamping the puncture needle. Therefore, it can be seen that the size of the puncture channel can be adaptive to a diameter of the puncture needle.

The two elastic walls 2211 in an embodiment of the present invention may be substantially in a shape of a pair of brackets, or additionally, may be further in a double-S or single-S shape or in other shapes, provided that a resilient force pointing to the first elastic wall can be produced. In addition, the first guiding wall 211 in the accompanying drawings may be in a shape of a rectangular plate, and the first guide wall 211 can also be curved slightly in a direction of the tension plate 221 or the needle groove plate 222. In a case that the first guiding walls 211 are curved slightly to the left or the right in the view in FIG. 8, a side of the section of the puncture channel 80 is correspondingly in the shape of an arc.

According to the technical solutions in the embodiments of the present invention, the needle groove plate has the elastic component, capable of forming the puncture needle having a size adaptive to the needle diameter of the puncture needle. Mounting walls on depth blocks of the different puncture guiders may be differed, thereby achieving puncture channels at various angles. The design of perpendicularity of the first guiding wall and the second guiding wall facilitates an operator to conveniently drive the first guiding wall with his fingers to open the puncture channel, so that the puncture needle can be easily taken out of the puncture channel.

The foregoing specific embodiments constitute no limitation on the protection scope of the present invention. A person skilled in the art should understand that, depending on design requirements and other factors, various modifications, combinations, sub-combinations, and substitutions may occur. Any modifications, equivalent replacements, or improvements made without departing from the spirit and principle of the present invention shall fall within the protection scope of the present invention.

The invention claimed is:

1. A puncture guider for connecting to a puncture support, characterized in that the puncture guider comprises a depth block and a push plate, wherein, the depth block comprises:
 a connection structure for being connected to at least one hook of the puncture support, the connection structure comprising a cylindrical ridge and two mounting walls parallel to each other, wherein the cylindrical ridge is connectable to a groove on a top of the at least one hook of the puncture support, wherein one or two of the mounting walls are provided with a protuberance, and wherein the protuberance is connectable to a U-shaped groove on the puncture support; and
 a first guiding wall and a second guiding wall which are connected to each other and form an included angle; and the push plate comprises:
 a needle groove plate; and
 an adaptive component which is an elastic component, the elastic component comprising a tension plate and two elastic walls, wherein the tension plate is fixedly connected to the needle groove plate through two connection rods, and wherein the tension plate, the needle groove plate, and the connection rod form a rectangle; and a first end of each of the two elastic walls connected to the tension plate, wherein an opposite end of the first end abuts against a first side of the first guiding wall, a push force of the elastic walls point to a second side of the first guiding wall, and a puncture channel is located at the second side of the first guiding wall;

the elastic walls are provided in a shape of a pair of brackets; wherein a first end surface of the needle groove plate, and the first guiding wall and the second guiding wall enclose the puncture channel, and, under an action of the adaptive component, a displacement occurs between the first end surface of the needle groove plate and the first guiding wall and second guiding wall, so that the puncture channel can change automatically according to a specification of a puncture needle, thereby automatically adapting to puncture needles with different needle diameter specifications.

2. The puncture guider according to claim 1, characterized in that the first guiding wall is located at a first side of the second guiding wall, is perpendicular to the second guiding wall, and is perpendicular to a first edge of the second guiding wall;

the cylindrical ridge is parallel to and connected to the first edge of the second side of the first guiding wall; and the mounting walls extend from the second side of the second guiding wall in a direction away from the second guiding wall.

3. The puncture guider according to claim 1, characterized in that the first end surface of the needle groove plate is an inclined plane in a shape of a slope, thereby enclosing the puncture channel having a triangular cross section with the first guiding wall and the second guiding wall.

4. A puncture guiding system, comprising a puncture support and the puncture guider according to claim 1, wherein, the puncture support comprises an annular puncture support body and the at least one hook fixed on the puncture support body; and the at least one hook is configured to cooperate with the connection structure on the puncture guider to connect the puncture guider on the puncture support.

5. The puncture guiding system according to claim 4, characterized in that each of two ends at an opening of the puncture support is provided with a connecting port;

the puncture guiding system further comprises a lock for connecting to both the two connecting ports in a non-detachable manner, so that the puncture support is formed into a closed ring shape; and the lock is provided with a weak part, wherein the lock can be torn apart from the weak part, thereby destroying the puncture support.

6. The puncture guiding system according to claim 5, characterized in that the weak part is formed by one or more rows of spaced holes on the lock.

7. The puncture guiding system according to claim 5, characterized in that the top of the at least one hook is provided with the groove, capable of rotationally connecting to the cylindrical ridge of the puncture guider;

two hook walls parallel to each other are provided under the top of the hook, and are perpendicular to a extending direction of the groove in the top of the hook; and each of the hook walls are provided with a respective U-shaped groove, capable of slidably connecting to the protuberance on respective a mounting wall of the puncture guider.

8. The puncture guiding system according to claim 4, characterized in that the top of the at least one hook is provided with the groove, capable of rotationally connecting the cylindrical ridge of the puncture guider;

two hook walls parallel to each other are provided under the top of the hook, and are perpendicular to a extending direction of the groove in the top of the hook; and each of the hook walls are provided with a respective U-shaped groove, capable of slidably connecting to the protuberance on respective a mounting wall of the puncture guider.

9. The puncture guiding system according to claim 4, characterized in that the first guiding wall is located at a first side of the second guiding wall, is perpendicular to the second guiding wall, and is perpendicular to a first edge of the second guiding wall;

the cylindrical ridge is parallel to and connected to the first edge of a second side of the second guiding wall; and the mounting walls extend from the second side of the second guiding wall in a direction away from the second guiding wall.

10. The puncture guiding system according to claim 4, characterized in that the first end surface of the needle groove plate is an inclined plane in a shape of a slope, thereby enclosing the puncture channel having a triangular cross section with the first guiding wall and the second guiding wall.

* * * * *